US012052509B2

(12) United States Patent
Schneider

(10) Patent No.: US 12,052,509 B2
(45) Date of Patent: Jul. 30, 2024

(54) SURFACE TOPOGRAPHY IMAGING SYSTEM

(71) Applicant: Sonoco Development, Inc., Hartsville, SC (US)

(72) Inventor: Greg W. Schneider, Florence, SC (US)

(73) Assignee: Sonoco Development, Inc., Hartsville, SC (US)

( * ) Notice: Subject to any disclaimer, the term of this patent is extended or adjusted under 35 U.S.C. 154(b) by 152 days.

(21) Appl. No.: 17/946,874

(22) Filed: Sep. 16, 2022

(65) Prior Publication Data

US 2023/0107551 A1 Apr. 6, 2023

Related U.S. Application Data

(60) Provisional application No. 63/251,314, filed on Oct. 1, 2021.

(51) Int. Cl.
| | |
|---|---|
| *H04N 7/18* | (2006.01) |
| *G01N 33/34* | (2006.01) |
| *G06T 7/00* | (2017.01) |
| *G06T 7/40* | (2017.01) |
| *H04N 23/74* | (2023.01) |

(52) U.S. Cl.
CPC ............ *H04N 23/74* (2023.01); *G01N 33/346* (2013.01); *G06T 7/0004* (2013.01); *G06T 7/40* (2013.01); *G06T 2207/10024* (2013.01); *G06T 2207/20132* (2013.01); *G06T 2207/30124* (2013.01)

(58) Field of Classification Search
CPC ........ H04N 23/74; H04N 7/18; G06T 7/0004; G06T 7/40; G06T 2207/10024; G06T 2207/20132; G06T 2207/30124; G01N 33/346

USPC ........................................................... 348/92
See application file for complete search history.

(56) References Cited

U.S. PATENT DOCUMENTS

| | | | | |
|---|---|---|---|---|
| 5,162,660 A | * | 11/1992 | Popil | G01N 21/57 356/600 |
| 5,598,006 A | | 1/1997 | Stringa | |
| 5,684,707 A | * | 11/1997 | Rogowski | G01N 33/346 73/159 |
| 5,854,683 A | * | 12/1998 | Keane | G01N 21/8983 356/238.1 |
| 5,899,595 A | * | 5/1999 | Verlinden | G03D 3/06 396/626 |

(Continued)

FOREIGN PATENT DOCUMENTS

| | | |
|---|---|---|
| GB | 2304195 A | 3/1997 |
| JP | 2009092657 A | 4/2009 |
| KR | 101516642 B1 | 5/2015 |

OTHER PUBLICATIONS

The World's First Affordable 3D Profilometer: Profilm3D, KLA Corporation, 4 pages, at site: https://www.filmetrics.com/profilometers/profilm3d?gclid=CjwKCAjwwab7BRBAEiwAapqpTKu9YsbjxGHvO71nOyoMJZaUzKvw6wQte2RkEEyvGjuz-bqe9kYGuBoCVPsQAvD_BwE.

(Continued)

*Primary Examiner* — Trang U Tran
(74) *Attorney, Agent, or Firm* — von Briesen & Roper, s.c.

(57) ABSTRACT

A system and method of obtaining a quantitative evaluation of paper. By looking at the topographic data and comparing it to machine parameters, an operator can optimize the paper forming machine settings to create consistently high quality paper with minimal surface defects.

15 Claims, 9 Drawing Sheets

(56) References Cited

U.S. PATENT DOCUMENTS

| | | | | |
|---|---|---|---|---|
| 6,188,077 B1* | 2/2001 | Lind | ................... | G01N 33/346 |
| | | | | 356/429 |
| 6,219,141 B1* | 4/2001 | Perrault | .............. | G01B 21/065 |
| | | | | 356/429 |
| 6,301,373 B1* | 10/2001 | Bernie | ................ | G06V 10/993 |
| | | | | 382/108 |
| 6,317,204 B2* | 11/2001 | Haga | ................... | G01B 11/306 |
| | | | | 356/600 |
| 6,504,617 B2 | 1/2003 | Komulainen et al. | | |
| 6,549,286 B2 | 4/2003 | Komulainen et al. | | |
| 6,947,150 B2 | 9/2005 | Rucker et al. | | |
| 7,969,565 B2 | 6/2011 | Stoeber | | |
| 8,654,349 B2 | 2/2014 | Bostrom | | |
| 9,798,130 B2 | 10/2017 | Dresel et al. | | |
| 10,089,532 B2* | 10/2018 | Loui | ..................... | G06V 20/46 |
| 2009/0060316 A1 | 3/2009 | Ruuska | | |
| 2020/0299082 A1 | 9/2020 | Seki | | |

OTHER PUBLICATIONS

OpTest Equipment Inc. "OpTiSurf" 900 Tupper St. Hawesbury, ON Canada, 2 pages, at site: http://www.optest.com/LFA06.htm.

Analytical methods for structure characterization of printing material "Modern methods for determination of paper surface typography" A. Hladnik, G. Chinga, A. Suhadolnik, 22 pages, at site: https://studylib.net/doc/7459011/optical-methods-for-determination-of-paper-surface-topogr . . . .

International Search Report and Written Opinion related to Application No. PCT/US2022/043424; reported on Jan. 6, 2023.

* cited by examiner

SURFACE TOPOGRAPHY IMAGING SYSTEM

BACKGROUND OF THE INVENTION

Field of the Invention

This disclosure relates to measuring the surface qualities of a substrate such as paper. More particularly, this disclosure relates to a method and apparatus for measuring the surface topography of paper.

Description of the Related Art

The term "paper" may refer to any kind of matted or felted sheet of fibrous material. Paper (general term) includes two general subdivisions: paper (specific term) and paperboard. The distinction is not sharp, but broadly speaking, paperboard is heavier, thicker and more rigid than paper. In general, sheets having a thickness of 0.010 inch (0.0254 cm) or more are classified as paperboard.

Papers of particular interest for the technology described herein include papers used to make food packaging. Papers for food packaging frequently are printed on and/or coated with a gas and/or liquid barrier coating.

Paper manufacturing generally involves a series of steps, including the preparation of raw materials, pulping, stock preparation and sheet formation. Raw materials can include wood, agricultural fibers, organic fillers, chemicals and water/steam. The pulping step may be done by mechanical means, chemical means or both. During stock preparation, the pulp is treated and/or prepared so that it will mat or felt properly during the sheet formation step.

The sheet formation step may be accomplished with the use of a cylinder paperboard machine comprising a vat, a cylinder mold, a porous felt and a press. The prepared pulp flows into the vat where a low consistency mixture of hydrated fibers ("furnish") are picked up by the cylinder mold and then transferred to the felt. The cylinder mold is a large hollow roll covered with a wire screen. The cylinder mold contains an internal vacuum section, which facilitates the pick-up of fiber and water from the vat and subsequently removes excess water from the fiber mat after it is lifted out of the vat. In the vat, it is important to maintain adequate movement of the furnish mixture to maintain an even distribution of the fibers while still in the water phase. Improper fluid flow leading up to the point of fiber pick-up on the surface of the wire screen will result in the aggregation of fibers into tight bundles referred to as flocs. These flocs are picked-up on the wire and result in a fiber mat consisting of areas of high and low densification of fibers. A fiber mat with no flocs and an even distribution of fibers exhibits good formation. A fiber mat with a poor distribution of fibers and high variability in fiber densification across a given cross section of the mat exhibits poor formation. Poor fiber mat formation impacts the ability to evenly dewater and press the mat and results in an uneven surface topography which will negatively impact print quality and/or the distribution of coatings applied to the paper.

The cylinder mold's internal vacuum section ends before the point of contact with a porous felt. A traveling press felt, located above and pressed against the cylinder by a press roll, picks up the fiber web coming off the cylinder. The press felt may travel over successive cylinders molds, picking up more layers of fibers along the way before transferring the fibrous sheet to a press section.

The press section may comprise a series of presses, each having a pair of rolls for removing water and smoothing and compressing the sheet. Throughout this press step the sheet typically remains carried by a press felt. During the final sheet formation step, press felts can make streaks or create other imperfections in the surface topography of the paper. These imperfections can also result in poor printing quality or poor coating of the paper.

The surface topography resulting from these initial stages of fiber mat formation and subsequent dewatering can vary from one papermaking run to another, or even within a single run. A number of methods have been developed to measure the surface topography of a paper sheet, including laser profilometry and low angle light methods.

Laser profilometry involves the use of a laser to generate a focused light beam onto the surface of the paper and a photodetector to accurately determine the shape and intensity distribution of the light spot on the detector. However, the equipment can be very expensive. In addition, the equipment may not properly hold down the paper samples during measuring and/or testing, resulting in the need for correcting software to reduce the impact of the waviness profile on the surface topographical data. Unfortunately, this software correction is not consistent from sample to sample and may induce testing error.

Low level light methods involve capturing single images of the paper surface while it is exposed to low angle light. One drawback to this method is that it can create variations in light exposure and contrast across the paper sample, which reduces testing accuracy for the surface topography characteristic(s) of interest and is difficult to correct for in image analysis software without impacting test accuracy. Furthermore, if the paper sample is not held down properly, large-scale waviness patterns due to paper dimensional stability will impact the ability to accurately capture the surface topography.

The present disclosure is designed to solve the problems described above.

BRIEF SUMMARY OF THE INVENTION

This disclosure relates to a system and method of obtaining a quantitative evaluation of the surface topography of paper made over the course of a single papermaking run or separate papermaking runs. By looking at the topographic data and comparing it to machine operating parameters, the operator can optimize the machine settings to create consistently high-quality paper with minimal surface defects.

Typical operating parameters that can be correlated to formation-based surface defects include refiner loading, dosage of retention/drainage chemistries, cylinder former or headbox stock dilution, machine speed, wet-end vacuum set points, jet/wire setpoint, jet impingement point, jet angle, selective use of dandy or lumpbreaker rolls, press felt vacuum level, press felt cleanliness or defects, and press loading.

In one aspect of the disclosure a system for measuring a quality of a paper sample is provided. The system may comprise a sample platform for holding the paper sample, a light source, a camera platform upon which a camera is mounted, a computer and panoramic image capture software. The sample platform ensures that the paper sample passes across a camera viewing area in a straight line and prevents y-directional shifting or rotation of the paper sample as images are simultaneously captured and interlaced via the camera's panoramic software. The light source may be mounted a first distance from the paper sample for casting low angle light onto the surface of the paper. The light source creates an even distribution of light across a length of the surface while the paper sample is moved with respect to the camera across the camera viewing area. The camera is mounted a second distance above the sample platform and is configured to take images of the paper sample as it passes across the camera viewing area. The computer is configured to receive the images using the panoramic image capture software and determine the quality of the paper sample using image analysis software. The sample platform may be equipped with a vacuum assisted bed to hold the paper sample securely against the sample platform in a relatively flat configuration. Optional clamps may be used to help hold the paper sample against the sample platform.

In another aspect of the disclosure a method of determining the surface topography of a paper sheet is provided. The method may comprise the steps of:

Positioning a paper sample on a sample platform and creating a vacuum under the sample platform to pull the paper sample against the sample platform.

Further securing the paper sample to the sample platform using edge plates and clamps.

Advancing the paper sample across a camera viewing area in a straight line.

Creating a real color panoramic image comprising one or more interlaced images of the surface of the paper sample using a camera and panoramic image capture software.

Cropping the real color panoramic image to create a usable image.

Converting the usable image into a greyscale data array.

Filtering out extreme data points from the greyscale data array to obtain a filtered greyscale data array that will provide usable surface topography data of the paper sample.

And converting the filtered greyscale data array into surface topography data using texture analysis software.

The method may include analyzing the filtered greyscale data array variability and producing a quantified average waviness value.

The surface topography data may be average waviness, void volume, valley volume or other useful data. If the paper sample has a waviness pattern, the surface topography data may be the directionality of the waviness pattern.

The method may include the additional step of providing the sample platform with sliding capabilities with respect to the camera.

The method may include the additional step of providing software that can inform an operator if the paper sample is moving too fast or too slow.

The method may include the additional step of maintaining a constant distance between the light source and the camera viewing area. This may be accomplished by activating the camera, moving the paper sample across the camera viewing area beginning at or about a leading edge of the paper sample and ending with a trailing edge, and deactivating the camera.

DETAILED DESCRIPTION OF THE INVENTION

Figure 1:
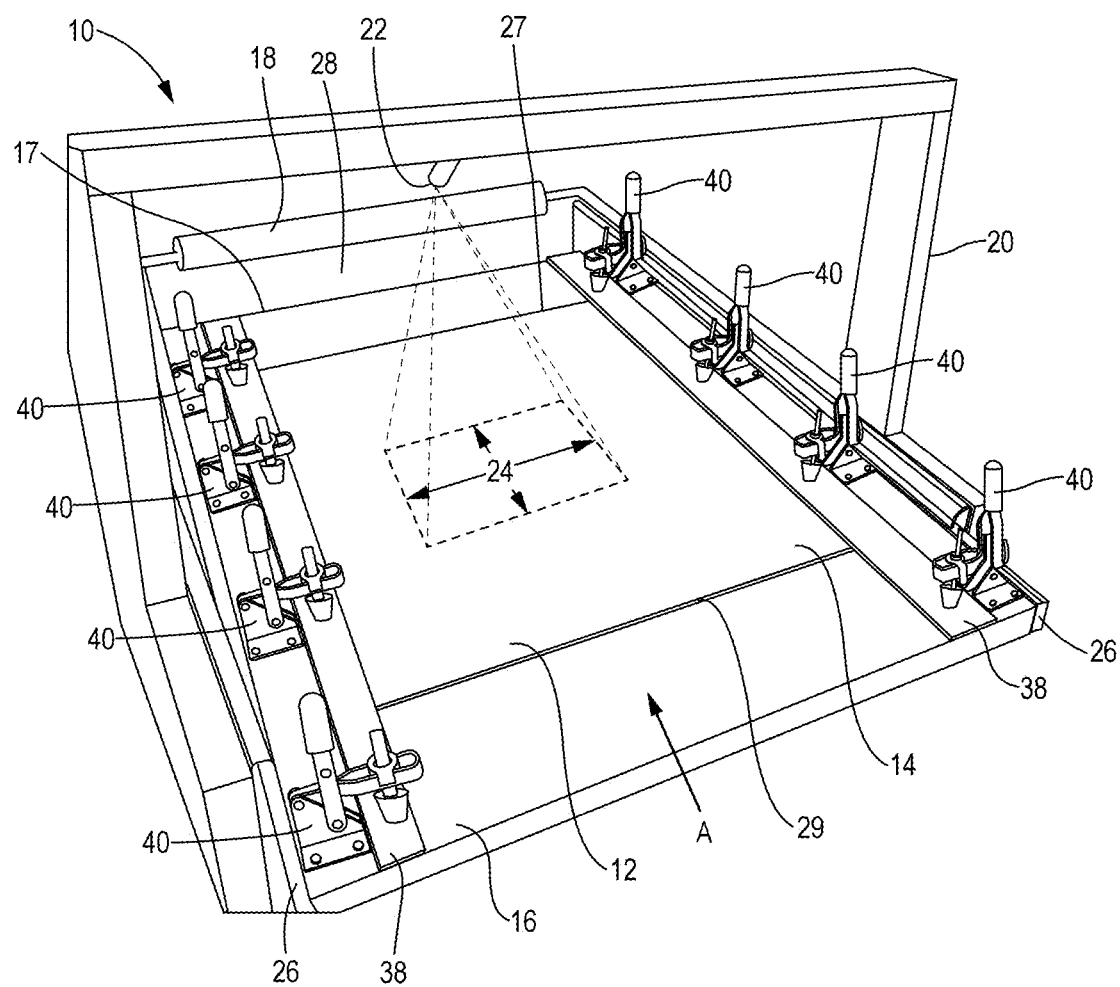
FIG. 1 is a perspective of a system for determining the surface topography of a paper sheet according to the disclosure.

While the invention described herein may be embodied in many forms, there is shown in the drawings and will herein be described in detail one or more embodiments with the understanding that this disclosure is to be considered an exemplification of the principles of the invention and is not intended to limit the disclosure to the illustrated embodiments. Aspects of the different embodiments can be combined with or substituted for one another.

As will be appreciated, terms such as "above" and "side" (etc.), used as nouns, adjectives or adverbs refer in this description to the orientation of the system as it is illustrated in the various views. Such terms are not intended to limit the invention to a particular orientation.

This disclosure relates to a system and method of obtaining a quantitative evaluation of the surface quality of paper made during an entire papermaking run. By looking at the topographic data and comparing it to machine parameters, the operator can optimize the machine settings to create consistently high-quality paper with minimal surface defects.

Definitions

Topography refers to the shape and geometric features of an object, such as the top or bottom surface contour of a sheet of paper.

Surface roughness refers to small-scale variations in the height of the surface topography. For example, roughness for a sheet of paper can be measured within a 0.5 inch (1.27 cm) cross section of sample. Paper machine factors affecting surface roughness typically include fiber quality and average length, refining influence on fiber length and fibrillation, forming wire design, the use of a top wire former, dandy roll or lumpbreaker roll, press felt design, dryer fabric design, smoothness of press roll and calendar rolls, and the tightness of the paper web as it is drawn through the paper machine.

Average surface waviness, abbreviated "Sa", aka average surface texture, is the measurement of most interest in the present system and method. Average surface waviness, as it relates to this disclosure, refers to larger scale variations in surface height across a larger cross section of the sample and allows identification and measurement of the frequency and height of surface irregularities measuring 0.2 inches to 1.0 inches (0.508 cm to 2.54 cm) in cross sectional diameter. Variations in surface waviness typically result from paper machine operating variables that influence the distribution of fibers within the dilute stock stream that approaches the forming section of the paper machine and how well the fibers remain distributed once applied to the medium that supports the fibers as water is removed from them through gravity, vacuum, and pressing stages.

Natural paper waviness relates to paper curl or warp resulting from variations in moisture level and/or fiber dimensional stability across a large paper sample.

Galvanization is paper surface condition that results from localized areas of high and low densification of fibers and can be identified visually by surface contour differences and patches of higher and lower color density across the sample.

I. System 10 for Obtaining an Image of a Surface 12 of a Paper Sample 14 and Measuring a Quality of the Paper Sample 14.

Turning to the drawings, where like numerals indicate like elements, there is shown in FIG. 1 one embodiment of the present invention, a surface topography imaging system 10 for obtaining an image of a surface 12 of a paper sample 14 and measuring a quality of the paper sample 14, such as texture.

The system 10 may comprise a sample platform 16 for holding the paper sample 14, a light source 18, a camera platform 20, an image capture device such as a camera 22 and a computer (not shown).

The paper sample 14 has a natural moisture content which may be anything from 4 wt % to 8 wt %. As air is drawn through the paper sample 14 during the process of determining paper topography described herein, the vacuum holding down the paper sample 14 can create a moisture differential within the paper sample 14, which can cause the paper sample 14 to wave or curl, especially at the leading edge 27 or trailing edge 29 of the paper sample 14. Curling of the leading edge 27 is particularly troublesome because it can interfere with the light directed at the paper sample 14, resulting in shadows cast across the sample which will impact image color data and surface topography measurement results. To prevent this from happening, the paper sample 14 can be held down on the sample platform 16 while a vacuum is drawn until any waviness or curling due to moisture is eliminated. A visual inspection may suffice for this purpose.

The sample platform 16 may be a double railed sliding platform 16, that is, a platform equipped along either side with cabinet or drawer rails 26, or other guide means (such as a crank operated cog track) that allows the sample platform 16 to move linearly back and forth as needed. This linear movement ensures that the paper sample 14 passes across a camera viewing area 24 in a straight line and that rotational movement of the paper sample 14 does not occur as images are being captured by the camera 22.

Figure 2:
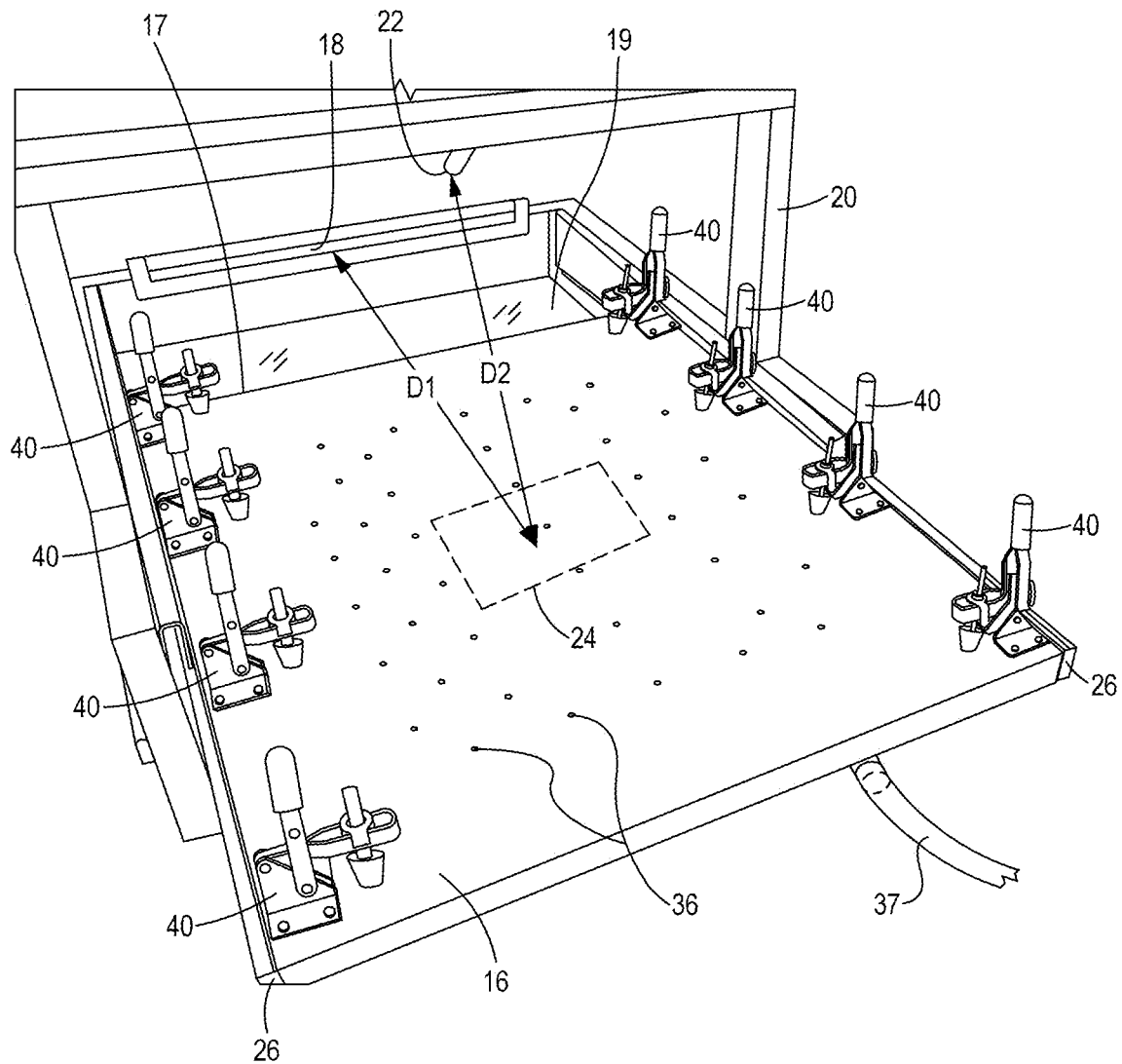
FIG. 2 is a perspective view of the system of FIG. 1 without the paper sample.

As better shown in FIG. 2, the sample platform 16 may define a plurality of tiny holes 36 arrayed across the platform 16. The holes 36 communicate with an enclosed hollow space located underneath the sample platform 16, which in turn communicates with a vacuum line 37 connected to a vacuum pump (not shown). The vacuum pump draws a vacuum through the holes 36, which helps hold the paper sample 14 against the sample platform 16 in a relatively flat configuration to reduce or eliminate any waviness of the paper sample. Typically, the vacuum pump will pull about ten inches (25.4 cm) (Hg) or more of vacuum; more for a particularly porous paper sample.

The light source 18 may be mounted in a stationary relationship with respect to the camera platform 20 and the camera 22. The light source 18 may be located a first distance (D1) from the camera viewing area 24 so that it casts a low angle light onto the surface 12 of the paper sample 14 as it passed through the camera viewing area 24. The light source 18 creates an even distribution of light across a length (L) of the surface 12 while the paper sample 14 is moved with respect to the camera 22 across the camera viewing area 24. The light source 18 may be a wide profile low angle LE) light with narrow light spacing.

An optional light reflecting structure 19 may be used. As shown in FIG. 1, when the sample platform 16 is in its initial position, away from the light source 18, there may exist a gap 28 or space between the light source 18 and the front (leading edge) of the sample platform 16. Light entering this gap 28 is mostly lost. In order to obtain a more even light exposure on the paper sample 14 during the entire movement of the sample platform 16, a light reflecting structure 19, such as a flat piece of filler material with similar light reflective properties to the sample platform 16 itself, may be mounted adjacent the front edge 17 of the sample platform 16 to fill in this gap 28, as shown in FIG. 2.

The camera platform 20 is designed to hold the camera 22 a set distance (D2) above or from the paper sample 14. This distance is a function of the desired dimensions of the camera viewing area 24, such as 6 inches by 6 inches (15.24 cm by 15.24 cm). Tape, clamps or other means may be used to hold the camera 22 in place.

The system 10 may further comprise one or more edge plates 38 and clamps 40 such as manual hold down clamps 40 to help hold the paper sample 14 against the sample platform 16 in a relatively flat configuration. Preferably the edge plates 38 and clamps 40 are black, painted black or covered in black material so that they do not cast light reflections onto the camera viewing area 24 of the paper sample 14. Alternatively, these light reflections can be mitigated by increasing the distance from the edge plates 38 and clamps 40 to the camera viewing area 24, something that could be accomplished by widening the sample platform 16 and, in turn, the paper sample 14.

The camera 22 is configured to take multiple images of the paper sample 14 as the sample 14 moves through the camera viewing area 24. The camera 22 is mounted a second distance (D2) above the sample platform 16 to ensure the size to pixel ratio of each image is consistent from test to test and to ensure that the second distance (D2) (from the camera 22 to the paper sample 14) is constant from test to test.

It has been found that the contrast provided by the placement of the camera 22 in a shielded position is better than when the camera 22 is exposed to the light source 18. Therefore, it is preferred that a shield (not shown) is positioned between the camera 22 and the light source 18. The camera 22 may be hooked up via a hard line connection or wireless connection to a separate device such as a laptop computer (not shown in the figures) or other computer.

Among numerous commercially available cameras with panoramic image capturing capabilities, Apple iPhone™ and Kodak™ brand cameras are preferred. Other cameras splice images together to create a panoramic image. Instead of splicing multiple images together to create a panoramic image, the preferred Apple iPhone and Kodak brand cameras interlace individual pixels of data as the paper sample 14 moves through the camera viewing area 24 in order to obtain consistent light exposure along the x-axis of the image, i.e., in the direction of travel of the paper sample 14.

Another advantage of the iPhone™ is that it has software that can warn the operator if the paper sample 14 is moving too fast across the camera viewing area 24. This excessive speed problem can be mitigated or eliminated by using a motor 124 with an adjustable speed setting as discussed below with respect to FIG. 3.

The computer is configured to receive the images and process that data to provide information to determine the quality of the paper sample. For example, the computer may receive the panoramic image 30 created by the camera 22 and convert it into an R, G, B color image, then convert the R, G, B color image into a matrix of greyscale equivalent numerical values.

Panoramic image capture software may be installed in the computer or in the camera 22 itself for obtaining a plurality of interlaced images of the surface 12 of the paper sample 14 while the sample 14 passes through the camera viewing area 24, and then converting the interlaced images into a single panoramic image 30.

Imaging software (such as Microsoft Paint™) may be installed in the computer for cropping the panoramic image.

Texture analysis software may be installed in the computer to convert the cropped panoramic image 32 into a usable greyscale format to view and analyze a data array represented by image 46. For example, the texture analysis software may convert R, G, B color images into an array of greyscale equivalent values from 0 to 255, which allows variability of the data in the array to be measured in both the x and y directions and averaged across the entire paper sample 14 to provide a waviness measurement. The texture analysis software 44 may be OmniSurf3D software, available from Digital Metrology Solutions.

Figure 3:
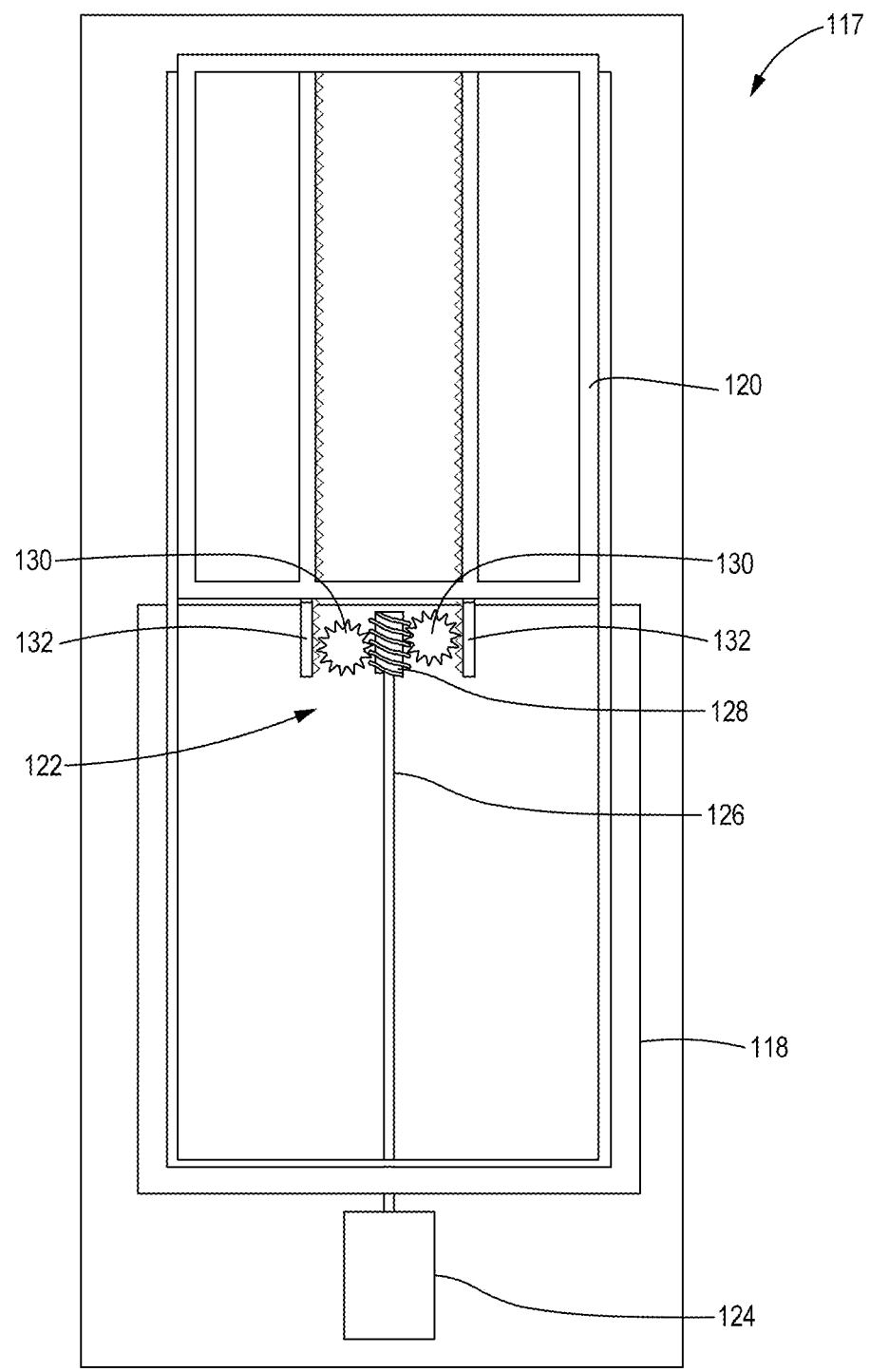
FIG. 3 is a top schematic view of a screw type mechanism that can be used to move a sample platform according to the disclosure.

The system may further comprise means for moving the paper sample 14 steadily across the camera viewing area 24 at an acceptable rate of speed. FIG. 3 is a top view schematic of one embodiment of a platform moving system 117 that can be used to move the sample platform 16 (removed for clarity) linearly back and forth across the camera viewing area 24. The platform moving system 117 is a screw type system comprising a stationary box 118, a moveable frame 120 upon which the sample platform 16 may be affixed, a screw assembly 122 and a motor 124.

The moveable frame 120 is operably connected to or mounted to the stationary box 118 and may move reciprocally back and forth with respect to the stationary box 118. The screw assembly 122 comprises a drive shaft 126 rotatably attached to the motor 124, a lead screw 128 attached to the shaft 126 at an end opposite the motor 124, two translational screws 130 operably attached to the lead screw 128, and nut rails 132 operably engaged to the translational screws 130 and fixedly attached to the moveable frame 120. The motor 124 drives rotational movement of the lead screw 128 in either a right handed or left handed direction. The lead screw 128 in turn drives the translational screws 130, which in turn move the frame 120, and thus the sample platform 16, in a linear direction.

II. Method for Obtaining an Image of a Surface 12 of a Paper Sample 14 and Measuring a Quality of the Paper Sample 14.

Figure 4:
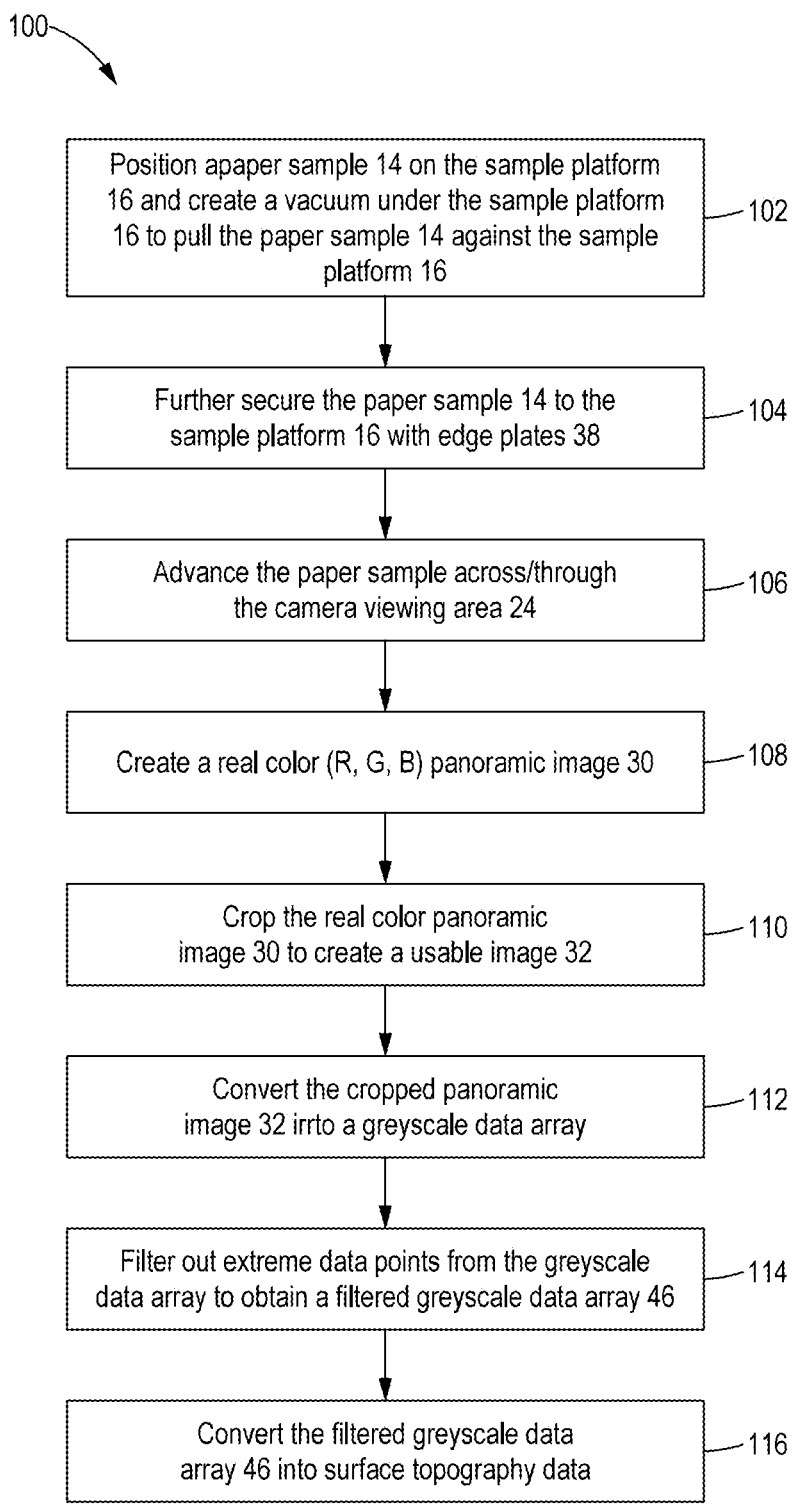
FIG. 4 is a flowchart depicting a representative embodiment of a method of determining the surface topography of a paper sheet according to the disclosure.

In another aspect of this disclosure, a method 100 of obtaining an image of a surface 12 of a paper sample 14 and measuring a quality of the paper sample 14 is provided. FIG. 4 is a flowchart depicting a representative embodiment of a method 100 of determining the surface topography of a paper sheet 14 according to the disclosure. The method 100 may comprise the following steps.

Step 102. Position a paper sample 14 on the sample platform 16 and create a vacuum under the sample platform 16 to pull the paper sample 14 against the sample platform 16. Paper is naturally wavy, and that natural waviness must be compensated for before or during testing. If the operator does not work to remove the waviness from the center of the paper sample 14 out to the edges, there is the potential to trap some of the waviness within the camera viewing area 24. Imaging software exists that can "remove" the waves through a set of filters, but the software is expensive. Accordingly, in a first step 102, a vacuum is created in an enclosed space underneath the sample platform 16, pulling the paper sample 14 against the platform 16, to help secure the paper sample 14 to the sample platform 16 in a flat orientation. The vacuum space may comprise multiple panels of wood or other relatively airtight material held together with adhesive and a sealant for sealing any gaps. The sample platform 16 may define numerous small vacuum holes 36 through which the vacuum is drawn.

Step 104. Further secure the paper sample 14 to the sample platform 16 with edge plates 38. In a first step 102, a paper sample 14, or "retain", that has been cut from a roll of paper is secured to the sample platform 16. Edge plates 38 and clamps 40 may be used to help secure the sides of the paper sample 14 to the sample platform 16 as shown in FIG. 1. The paper sample 14 may be positioned such that each of its side edges is located between the sample platform 16 and one of a pair of edge plates 38, then each of the edge plates 38 may be held in position by one or more clamps 40.

The paper sample 14 can be any suitable size, such as 6 inches by 6 inches (15.24 cm by 15.24 cm) or 12 inches by 12 inches (30.48 cm by 30.48 cm). Multiple paper samples 14 may be obtained and tested from a single roll of paper. Typically, a set of eight paper samples 14 is retained from a single roll. A number of tests may be conducted on each retain and the quality data stored for future reference in case of customer complaints, etc.

Surface topography tests have been performed using various orientations of the paper sample 14 relative to the light source 18, for example, by obtaining four test results per paper sample 14: two tests across the left and right cross directions and two tests across the leading and trailing machine directions.

Step 106. Advancing the paper sample across/through the camera viewing area 24. In a next step 106, the paper sample 14 is advanced across a camera viewing area 24 in a straight line without the paper sample 14 shifting vertically (up or down) or laterally (side to side). This strictly linear movement may be accomplished by providing the sample platform 16 with sliding capabilities with respect to the camera 22. The sample platform 16 can be slid (moved) manually or with equipment. The camera 22 may have software that can inform the operator whether the paper sample 14 is moving too fast or too slow.

Step 108. Creating a real color (R, G, B) panoramic image 30. In a next step 108, a panoramic image 30, that is, a photo comprising one or more interlaced images of the surface 12 of the paper sample 14, is created by the camera 22 using panoramic image capture software installed in a computer located within or outside of the camera 22. This panoramic image generating technique provides a consistent exposure of light across the entire paper sample 14, since the distance between the light source 18 and the camera viewing area 24 never changes.

Referring to FIG. 1, this step may be accomplished by activating the camera 22 and then moving the paper sample 14 across the camera viewing area 24, beginning at or about a leading edge 27 of the paper sample 14 and ending with a trailing edge 29, then deactivating the camera 22.

As the paper sample 14 moves across the camera viewing area 24, the camera 22 adds numerous narrow pixel lines to the panoramic image 30. The panoramic image 30 created comprises the first pixel line created when the leading edge 27 of the paper sample 14 first enters the camera viewing area 24 (the "initial image"), plus the additional lines (columns) of pixels added to the initial image in the transverse (side to side) direction (orthogonal to the direction the paper sample 14 is moving) until the trailing edge 29 of the paper sample 14 exits the camera viewing area 24. The light exposure remains the same as the paper sample 14 moves through the camera viewing area 24.

For a 12×12 inch (30.48×30.48 cm) camera viewing area 24 (which is also the size of the panoramic image 30), the "width" of the image (in the linear travel direction) may be limited to about 10 inches (25.4 cm) and the "height" (in the side to side (rail to rail) direction) to about 8 inches (20.32 cm) to avoid any light reflections caused by the rails 26 or the edge plates 38.

The system 10 can accommodate complete image capture of 12"×12" (30.48×30.48 cm) paper samples 14, as well as smaller, 10" (25.4 cm) wide paper samples 14 in the direction of platform movement. It may be possible to accommodate larger paper sample sizes as well, as long as modifications are made to the system 10. For example, for larger paper samples 14, the sample platform 16 should be longer and the vacuum area expanded. Also, the vacuum area and the camera platform 20 may have to moved closer to the light source 18.

Figure 5:
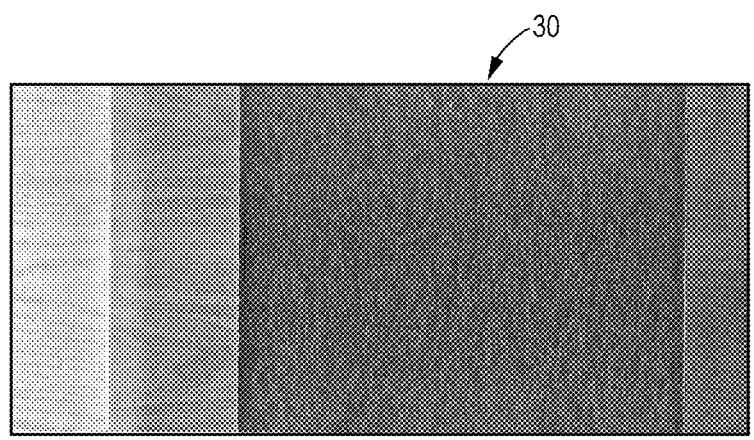
FIG. 5 is a greyscale reproduction of a real color panoramic image as it appears on a user's computer screen using Microsoft Paint™ software before cropping.

FIG. 5 is a greyscale reproduction of a real color panoramic image 30 as it might appear on a user's computer screen using Microsoft Paint™ software.

Figure 6:
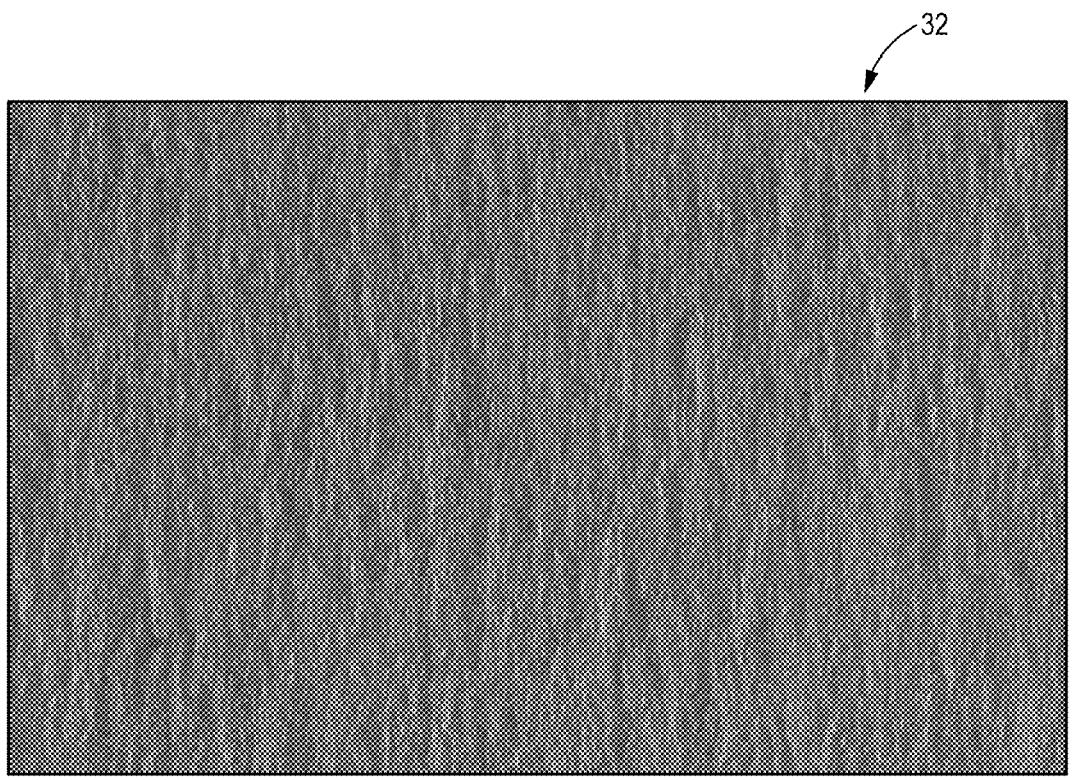
FIG. 6 is a greyscale reproduction of a real color panoramic image as it appears on a user's computer screen using Microsoft Paint™ software after cropping.

Step 110. Cropping the real color panoramic image 30 to create a usable image 32. In a next step 110, the panoramic image 30 is cropped into a usable form, image 32, to eliminate edge problems. This step can be accomplished using imaging software 42 (such as Microsoft Paint™). FIG. 6 shows the real color panoramic image 30 of FIG. 5 after it has been cropped into a usable image 32.

At the beginning of the imaging step 108, there may be light differentiation within the camera viewing area 24 because the sample platform 16 holding a large paper sample 14 cannot be moved completely through the camera viewing area 24. Thus, as an optional additional step, the operator can crop out those portions of the beginning or ending of the panoramic image 30 where the paper sample 14 cannot pass entirely through the camera viewing area 24 so the resulting panoramic image 30 is one having constant light conditions. Optionally, movement of the camera platform (20), lengthening of the sample platform (16) and/or increasing the number of vacuum holes (36) in the direction of movement of the paper sample 14 (arrow A in FIG. 1) to accommodate larger sample sizes will allow the operator to move the paper sample 14 completely into and out of the camera viewing area 24 to eliminate lighting variances at the beginning or end of the captured panoramic image 30.

The cropping step 110 may be accomplished as follows. The operator may utilize the Paint® software to manually select an area from within the sample image, copy that area, and create a new image file comprised only of that copied area. Alternately, an operator may use a program to analyze the matrix of pixel color values generated from an image file to automatically identify the position and size of the cropped area to be captured within a sample image. The operator may utilize an image analysis program such as ImageJ to transform an image into an array of greyscale pixel values. From each column of pixel values, an average value can be calculated from the total of all pixel values. The operator can calculate the standard deviation from a group of column averages along the real color image in the direction of travel and determine exactly where the left hand edge 27 of the paper sample 14 begins by identifying the point at which the standard deviation is greatest. The operator can then utilize the ImageJ software to identify the starting position of cropped image pixel data collection by counting a specific number of rows or pixels down from the top of the image and specific number of columns or pixels to the right of the leading edge 27. From that starting position, the operator can select the number of rows of pixel data to collect moving down the array and the number of columns of pixel data to collect moving across the array to the right. This array of selected data stored as a panoramic image 32 is saved and utilized as the cropped image data set to be used by the surface topography software in Steps 112 to 116.

Step 112. Converting the cropped panoramic image 32 into a greyscale data array. In a next step 112, the cropped panoramic image 32 is further processed using imaging software (such as OmniSurf3D) to either extract an array of greyscale values from the image data or to convert the real color (red, green, blue) data from the cropped panoramic image 32 into a single greyscale data array.

Step 114: Filtering out extreme data points from the greyscale data array to obtain a filtered greyscale data array 46 that will provide usable surface topography data of the paper sample 14. The greyscale data array 46 may be further manipulated in the OmniSurf3D software by filtering out extreme data points to obtain an array that will provide usable surface topography data of the paper sample 14. For example, the operator may instruct the computer to eliminate certain of the highest data values and the lowest data values, such as those exceeding three standard deviations. The highest data values may be filtered out because they are more indicative of white contamination in the paper sample 14 or fibers protruding from the paper sample 14. Similarly, the lowest values may be filtered out because they are more indicative of dark contamination in the paper sample, not the surface texture that the operator is seeking to measure. Wave pattern filters are also selected to focus the array analysis on only larger scale data variances that are more indicative of the waviness patterns of interest for particular surface topographical features. For qualitative evaluation purposes, the OmniSurf3D program creates a three-dimensional graphical representation of the greyscale data variations where z-directional data points correspond to high or low greyscale color values in the data array.

Figure 7:
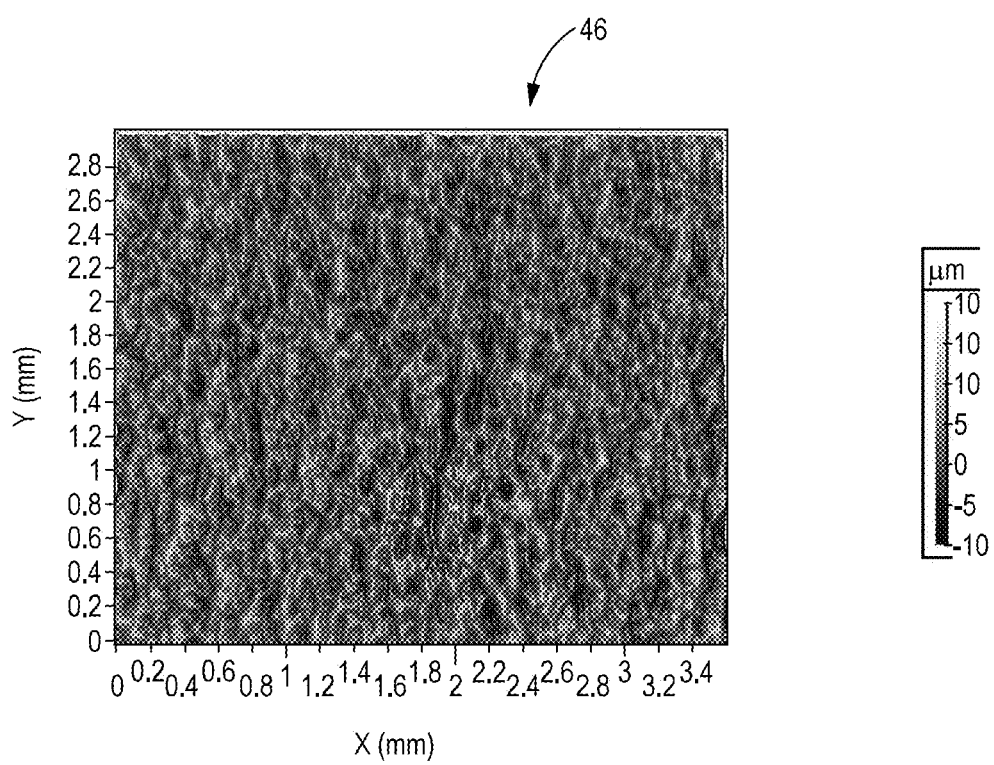
FIG. 7 is a top view graphic image generated from the cropped image of FIG. 6 after the cropped image has been filtered with the operator's data filtering settings.
Figure 8:
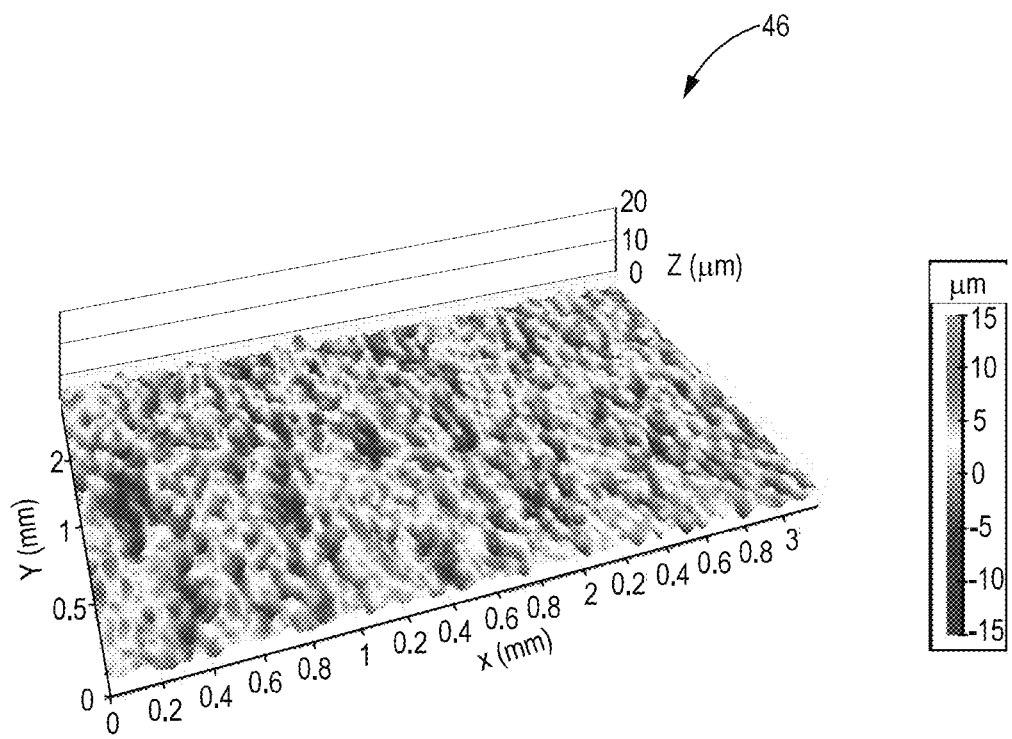
FIG. 8 is a perspective view of the graphic image of FIG. 7.

FIG. 7 is a top view greyscale data image 46 generated from the cropped image 32 of a paper sample after being filtered with the operator's data filtering settings. FIG. 8 is a perspective view of the same greyscale data image 46. The image 46 graphically depicts the variation of greyscale values across a portion of the paper sample 14. The image 46 utilizes a scale that is $\frac{1}{60}^{th}$ actual size measuring about 2.0 mm wide (Y scale) by about 3.2 mm long (X scale) by about 20 μm deep (Z scale). Image 46 shown in FIG. 7, as well as in FIGS. 8 and 9, is an example of this three-dimensional view of the post-analysis wave pattern data where peaks are associated with areas showing consistent high greyscale values and valleys are associated with areas of consistent lower greyscale values.

Figure 9:
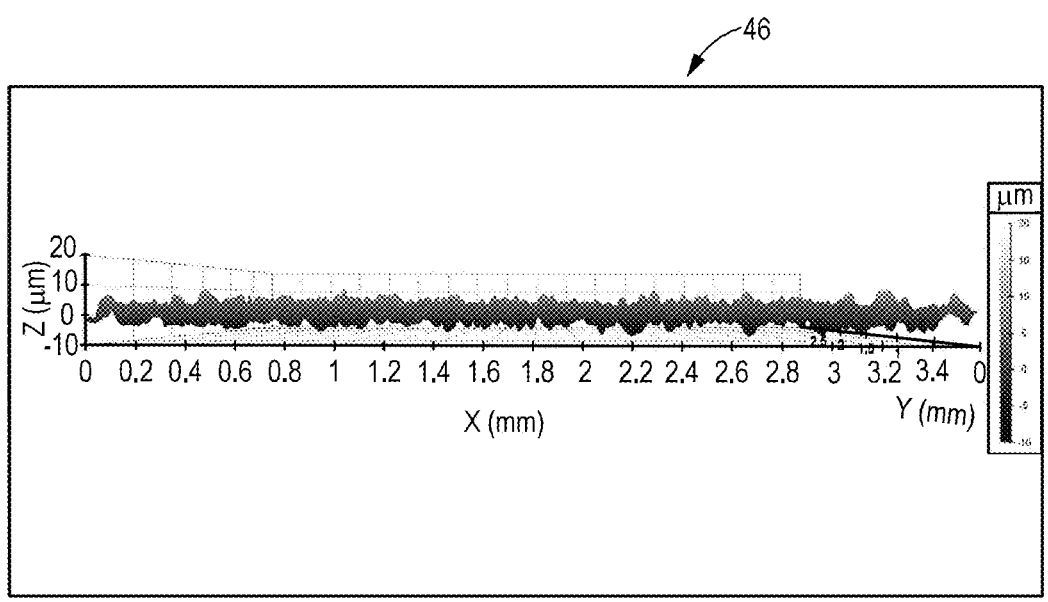
FIG. 9 is a cross sectional view of the graphic image of FIG. 7.

FIG. 9 is a cross-sectional ("edge on") view of the same image 46 in FIGS. 7 and 8. As perhaps best shown in FIG. 9, the highest calculated "peaks", measured in the number of micrometers (μ) above the mean plane (z=0) of the image 46, are about 10 micrometers (μ) and the lowest calculated "valleys" are about 10 micrometers (μ) below the mean plane of the image 46.

The steps 112 to 114 performed by the OmniSurf3D software involve extracting the grey-scale pixel value array from the image files or using the R, G, B color values from the cropped image files to create a greyscale data array from those values. After the greyscale data array is loaded, the program is set-up to automatically filter the data to exclude extreme values and then analyze the array based on specified wavelength (variability) detection limits and then calculate a surface topography waviness value. The real color (R, G, B) image illustrated in FIGS. 7, 8 and 9 is a three-dimensional representation of the variations or wave patterns analyzed in the filtered greyscale data array 46 and is not used for any subsequent steps.

Step 116. Converting the filtered greyscale data array 46 into surface topography data using texture analysis software. In a next step 116, the filtered greyscale data array 46 generated with the OmniSurf3D software is converted/analyzed using OmniSurf3D's texture analysis software to provide surface topography data, for example, texture measurements. This measurement may be accomplished by analyzing the filtered data variability shown graphically in image 46 of FIGS. 7, 8 and 9 and producing a quantified average waviness value, "Sa" value.

The variations in the 0 to 255 greyscale data array 46 provide a roughness or average waviness result, usually expressed in micrometers, based on patterns in the data that are interpreted as wave frequencies and amplitudes. Larger, more consistent variations in the data array correspond to larger calculated waviness values whereas smaller, less consistent variations correspond to smaller calculated waviness values. An operator can identify the surface topographical features of interest by focusing the analysis on longer wavelength patterns which exhibit higher amplitude variability.

For example, from the images of FIGS. 7, 8 and 9 the average waviness (Sa) was calculated to be 2.392 micrometers. Other topographical parameters may be measured as well. For instance, the void volume based on an 0%: 80% material ratio (Vvc) was calculated to be 0.317 micrometers. The valley volume via Kernel/Core Roughness analysis (Svo) was calculated to be 0.120 micrometers.

The operator can also determine the directionality of the waviness pattern in the original paper sample 14. For example, the panoramic image 30 in FIG. 5 appears to contain a number of deep grooves running in the Y (vertical) direction. The OmniSurf3D program allows the operator to calculate the aspect ratio of the surface features. The closer to zero the aspect ratio, the more directional the waviness (valley or peak) pattern. Accordingly, the operator can designate that the aspect ratio be above a certain limit, or else that paper sample test will be discarded.

From start to finish the entire method may take five minutes per paper sample 14. "Plug n play" operation is desired.

EXAMPLES

In one set of roughness tests, twelve paper samples were tested for waviness, total peak to valley height, and void volume relative to cut percent to determine which surface topography measurement provided the best correlation to variations in print test measurements.

The following table provides data for twelve samples taken from different paper making runs. The samples have been ranked from the best (Sample 1; 207 F) to the worst (Sample 12; 705 WB) based on the results of print tests previously performed on these samples. Of the different surface evaluation measurements used, the average waviness measurement provided the best relative correlation to the print test results.

| | Surface Evaluation Measurement | | | |
|---|---|---|---|---|
| Sample | Avg. Waviness | Total Peak to Valley Height | Void volume Relative to Cut Percent (80%) (Vvo) | Valley Volume (Svo) |
| 1 207F | 1.996 | 22.587 | 0.265 | 0.103 |
| 2 607F | 2.509 | 25.037 | 0.328 | 0.128 |
| 3 904MB | 2.657 | 28.943 | 0.345 | 0.131 |
| 4 607WB | 2.754 | 27.191 | 0.368 | 0.151 |
| 5 904M | 2.547 | 28.915 | 0.34 | 0.136 |
| 6 607MB | 2.855 | 26.794 | 0.365 | 0.126 |
| 7 904 | 3.51 | 34.468 | 0.451 | 0.169 |
| 8 607B | 3.218 | 38.563 | 0.129 | 0.171 |
| 9 705F | 3.875 | 32.546 | 0.454 | 0.144 |
| 10 705M | 3.711 | 36.656 | 0.462 | 0.162 |
| 11 705MB | 3.869 | 37.596 | 0.468 | 0.145 |
| 12 705WB | 4.338 | 36.757 | 0.521 | 0.171 |

Surface waviness is an undesirable quality, as noted above. Sample 1, with an average waviness value of 1.996, was considered the best sample in terms of waviness.

Waviness Index Usefulness

By testing the lowest and highest texture samples, an index can be created to use for comparison of one paper mill output to another. The index also can be used to compare different sheet materials. The index can also be used by customers as an objective measure of paper quality. The index may be expressed on a 0-100 scale or any desirable scale.

Thus there has been described a system and method of obtaining a quantitative evaluation of the surface topography of paper. By looking at the topographic data and comparing it to machine parameters, an operator can optimize the machine settings to create consistently high-quality paper with minimal surface defects.

It is understood that the embodiments of the invention described above are only particular examples which serve to illustrate the principles of the invention. Modifications and alternative embodiments of the invention are contemplated which do not depart from the scope of the invention as defined by the foregoing teachings and appended claims. It is intended that the claims cover all such modifications and alternative embodiments that fall within their scope.

The invention claimed is:

1. A system for measuring a quality of a paper sample, the system comprising:
    a sample platform for holding the paper sample and ensuring that the paper sample passes across a camera viewing area in a straight line and that rotation of the paper sample does not occur as images are being captured;
    a light source mounted a first distance (D1) from the camera viewing area for casting low angle light onto a surface of the paper sample;
    a camera configured to take a panoramic image of the paper sample placed in the camera viewing area;
    a camera platform for holding the camera, the camera mounted a second distance (D2) above the sample platform;
    a computer configured to receive the panoramic image from the camera and determine the quality of the paper sample; and
    panoramic image capture software for interlacing individual pixels of data to form the panoramic image of the surface while the paper sample is moved with respect to the camera viewing area; wherein the light source creates an even distribution of light across a length (L) of the surface while the paper sample is moved with respect to the camera across the camera viewing area.

2. The system of claim 1 wherein:

the light source is a wide profile low angle LED light with narrow light spacing.

3. The system of claim 1 wherein:

the sample platform defines a plurality of holes arrayed across the sample platform, the holes communicating with an enclosed hollow space located underneath the sample platform which communicates with a vacuum line connected to a vacuum pump in order to hold the paper sample against the sample platform in a relatively flat configuration.

4. The system of claim 1 further comprising:

a first edge plate located proximate a first edge of the sample platform and having a first side edge of the paper sample located between the sample platform and the first edge plate;

a second edge plate located proximate a second edge of the sample platform opposite the first edge and having a second side edge of the paper sample located between the sample platform and the second edge plate; and manual hold down clamps clamping the first edge plate and the second edge plate in position to hold the paper sample against the sample platform in a relatively flat configuration.

5. The system of claim 1 further comprising:

means for moving the paper sample steadily across the camera viewing area at an acceptable rate of speed.

6. The system of claim 1 further comprising a screw type sample platform moving system, the sample platform moving system comprising:

a stationary box;

a moveable frame operably connected to or mounted to the stationary box and configured to move reciprocally back and forth with respect to the stationary box; and a screw assembly comprising a drive shaft rotatably attached to a motor, a lead screw attached to the drive shaft at an end opposite the motor, two translational screws operably attached to the lead screw, and nut rails operably engaged to the translational screws and fixedly attached to the moveable frame; wherein the motor drives rotational movement of the lead screw in either a right handed or left handed direction, causing the sample platform to move in a linear direction.

7. A method of determining the surface topography of a paper sample, the method comprising the steps of:

Step (102): positioning the paper sample on a sample platform and creating a vacuum under the sample platform to pull the paper sample against the sample platform;

Step (104): further securing the paper sample to the sample platform using edge plates and clamps;

Step (106): moving the paper sample across a camera viewing area in a straight line;

Step (108): creating a real color panoramic image comprising one or more interlaced images of the surface of the paper sample using a camera and panoramic image capture software;

Step (110): cropping the real color panoramic image to create a usable image;

Step (112): converting the usable image into a greyscale data array;

Step (114): filtering out extreme data points from the greyscale data array to obtain a filtered greyscale data array that will provide usable surface topography data of the paper sample; and Step (116): converting the filtered greyscale data array into surface topography data using texture analysis software.

8. The method of claim 7 wherein step (116) comprises:

analyzing the filtered greyscale data array variability and producing a quantified average waviness value.

9. The method of claim 7 wherein the surface topography data of step (116) is average waviness.

10. The method of claim 7 wherein the surface topography data of step (116) is void volume and valley volume.

11. The method of claim 7 wherein the paper sample has a waviness pattern and the surface topography data of step (116) is a directionality of the waviness pattern.

12. The method of claim 7 including the additional step of:

providing the sample platform with sliding capabilities with respect to the camera.

13. The method of claim 7 including the additional step of:

providing software that can inform an operator if the paper sample is moving too fast or too slow.

14. The method of claim 7 including the additional step of:

maintaining a constant distance between the light source and the camera viewing area.

15. The method of claim 14 wherein the distance between the light source and the camera viewing area is maintained as a constant by the steps of:

activating the camera;

moving the paper sample across the camera viewing area beginning at or about a leading edge of the paper sample and ending with a trailing edge; and deactivating the camera.

* * * * *